(12) United States Patent
Misono

(10) Patent No.: US 7,905,839 B2
(45) Date of Patent: Mar. 15, 2011

(54) ULTRASONIC OBSERVATION APPARATUS

(75) Inventor: Kazuhiro Misono, Uenohara (JP)

(73) Assignee: Olympus Corporation, Tokyo (JP)

( * ) Notice: Subject to any disclaimer, the term of this patent is extended or adjusted under 35 U.S.C. 154(b) by 953 days.

(21) Appl. No.: 11/810,084

(22) Filed: Jun. 4, 2007

(65) Prior Publication Data

US 2008/0009744 A1 Jan. 10, 2008

Related U.S. Application Data

(63) Continuation of application No. PCT/JP2005/022198, filed on Dec. 2, 2005.

(30) Foreign Application Priority Data

Dec. 6, 2004 (JP) .................................. 2004-353426

(51) Int. Cl.
*A61B 8/00* (2006.01)
(52) U.S. Cl. ....................................... 600/462; 600/459
(58) Field of Classification Search .................. 600/459, 600/462
See application file for complete search history.

(56) References Cited

U.S. PATENT DOCUMENTS

| | | | |
|---|---|---|---|
| 4,674,515 A | 6/1987 | Andou et al. | |
| 5,209,235 A | 5/1993 | Brisken et al. | |
| 2002/0049375 A1 | 4/2002 | Strommer et al. | |
| 2002/0138007 A1 * | 9/2002 | Nguyen-Dinh et al. | 600/459 |

FOREIGN PATENT DOCUMENTS

| | | |
|---|---|---|
| FR | 1 366 879 A | 7/1964 |
| GB | 2 402 215 A | 12/2004 |
| JP | 61-103436 | 5/1986 |
| JP | 03-099644 | 4/1991 |
| JP | 11-276484 | 10/1999 |
| JP | 2000-296128 | 10/2000 |
| JP | 2002-315748 | 10/2002 |
| JP | 2002-315749 | 10/2002 |

OTHER PUBLICATIONS

Translation of JP 2002-0315749.*
Translation of JP 2000-296128.*
Japanese Official Action dated Aug. 17, 2010.

* cited by examiner

*Primary Examiner* — Brian Casler
*Assistant Examiner* — Jonathan G Cwern
(74) *Attorney, Agent, or Firm* — Scully, Scott, Murphy and Presser, P.C

(57) ABSTRACT

An ultrasonic probe to be inserted into a body cavity internally contains an ultrasonic transducer. An ultrasonic observation apparatus to which the ultrasonic probe is connected outputs transmit signals in a pulse shape. A cabinet of the ultrasonic observation apparatus is connected to a ground of a secondary circuit and is insulated is direct current from the ground of a patient circuit. The secondary circuit has a timing generating circuit generating timing signals for generating the transmit signals. An insulating circuit insulates the timing signals from the secondary circuit and transmits the timing signals to the patient circuit. The patient circuit has a transmit signal generating circuit generating the transmit signals in synchronization with the inputted timing signals.

8 Claims, 7 Drawing Sheets

ULTRASONIC OBSERVATION APPARATUS

CROSS REFERENCE TO RELATED APPLICATION

This application is a continuation application of PCT/JP2005/022198 filed on Dec. 2, 2005 and claims benefit of Japanese Application No. 2004-353426 filed in Japan on Dec. 6, 2004, the entire contents of which are incorporated herein by this reference.

BACKGROUND OF THE INVENTION

1. Field of the Invention

The present invention relates to an ultrasonic observation apparatus that generates transmit pulses suitable for exciting an ultrasonic transducer.

2. Description of the Related Art

In recent years, an ultrasonic observation apparatus is connected to an ultrasonic endoscope or an ultrasonic probe to perform a substantial diagnosis of the degree of submucosal invasion of a change or an organ.

The distal end of the ultrasonic endoscope or ultrasonic probe internally contains an ultrasonic transducer. The electric driving pulses transmitted from the ultrasonic observation apparatus and applied to the ultrasonic transducer are converted to acoustic ultrasonic pulses by the ultrasonic transducer and are irradiated to an internal tissue.

The reflected waves returned from the internal body are converted to electric signals by the ultrasonic transducer, undergo signal processing and are displayed as an ultrasonic tomographic image.

Conventionally, PZT (two-component system piezoelectric ceramics Pb(Ti,Zr)O3) transducer or a complex piezoelectric element is used as the ultrasonic transducer, and a driving method suitable for the ultrasonic transducer has been adopted.

For example, the fractional bandwidth of a conventional PZT transducer is about 70%, and pulses having a time slot of the center frequency are driven by about three burst waves (continuous waves) in order to use the PZT transducer efficiently.

The complex piezoelectric element has a significantly wide fractional bandwidth of 100% or larger, compared to a conventional PZT transducer.

In order to use such an ultrasonic transducer, the frequency band of transmit pulses largely has increasingly largely depended on an ultrasonic image thereof since the frequency bandwidth of the complex piezoelectric element is wider than the frequency bandwidth of the transmit pulse.

For example, THI (Tissue Harmonic Imaging) has gathered attentions as a method for improving the lateral resolution.

According to the technology, when ultrasonic signals of fundamental waves are transmitted from the ultrasonic transducer, the fundamental waves are distorted on a propagation path within a body, and second- and third-order harmonics occur.

Imaging extracted signals of the harmonics occurring in the internal body is called THI.

A technology for transmitting fundamental waves only to the internal body and a technology for receiving the harmonics occurring in the internal body are important for performing THI. Therefore, the ultrasonic transducer must have a wider fractional bandwidth, and an ultrasonic transmitting circuit that generates ultrasonic fundamental waves must have a configuration that prevents the occurrence of harmonics.

The ultrasonic observation apparatus has a problem unique to medical equipment.

An ultrasonic endoscope or ultrasonic probe must be inserted to the inside of a human body, and, in order to assure the security for a human being from the point of view, the standards relating to electric security on leak current and withstand voltage, for example, must be met.

In order to be satisfied with the standards on the leak current and withstand voltage, a conventional ultrasonic observation apparatus must have a patient circuit that floats a circuit to which an ultrasonic endoscope or ultrasonic probe is electrically connected, such as a transmitting circuit part from a primary circuit (commercial power supply) of the ultrasonic observation apparatus and a secondary circuit (including the apparatus cabinet) that operates the inside of the apparatus.

The ultrasonic observation apparatus must have the patient circuit and, at the same time, keep the amount of noise radiated to the outside of the apparatus (radiated electromagnetic noise) equal to or lower than a provided value.

The eradiated electromagnetic noise is restricted so as to prevent an adverse effect to equipment used in a medical organization, such as a pacemaker.

In order to reduce the radiated electromagnetic noise, the current to be supplied to the patient circuit must be kept as small as possible.

Weakening the electromagnetic noise by a current loop in a size reduced as much as possible within a circuit by reducing the circuit current is effective for reducing the radiated electromagnetic noise.

If the circuit can be grounded to the apparatus cabinet, like the secondary circuit, many ground points can be obtained, which reduces the value of the current loop and can thus reduce the amount of the radiated electromagnetic noise.

However, in the patient circuit that cannot be grounded to the apparatus cabinet, the value of the current loop is relatively higher.

Reducing the current to be used in the patient circuit is effective for reducing the amount of the radiated electromagnetic noise in the patient circuit, and the circuit current in conventional apparatus has not been increased.

While means for shielding the patient circuit by the apparatus cabinet, which is a ground (GND) for the secondary circuit may be employed without limiting the circuit current, the size of the apparatus itself increases, which is a problem.

Next, with reference to FIG. 7, a prior art by Japanese Unexamined Patent Application Publication No. 2002-315749 will be described. FIG. 7 is a timing chart showing a process of creating a transmit waveform.

An ultrasonic endoscope has a single ultrasonic transducer at the distal end of the endoscope.

The ultrasonic transducer is rotated about the axis of the endoscope insertion section by rotating rotational driving power, and radial scanning of ultrasonic wave is performed with the rotational scanning.

When the radial scanning is performed, a synchronizing signal (A-phase trigger) is transmitted from the ultrasonic endoscope to the ultrasonic observation apparatus in synchronization with the rotation of the ultrasonic transducer.

The A-phase trigger generates 512 pulses, for example, during one rotation of the ultrasonic transducer in the radial direction.

The ultrasonic observation apparatus supplies transmit signals (transmit pulses) in synchronization with the 512 pulses to the ultrasonic transducer, obtains received echoes thereof and creates one image.

In the prior art, transmit pulses of two burst waves are outputted by handling the A-phase trigger as the synchronizing signal.

The process for outputting two burst waves is shown in FIG. 7.

By handling the A-phase trigger in FIG. 7 as the synchronizing signal, a pulse of a uniform pulse width is created.

The generated pulses are sequentially delayed as the timing signals shown in FIG. 7 by eight delay elements (which will be abbreviated simply to "delay" below) D1 to D8.

The delays D1 and D2 create the first wave of the synthesized pulse P1.

The delays D5 and D6 create the second wave of the synthesized pulse P1.

The delays D3 and D4 create the first wave of the synthesized pulse P2.

The delays D7 and D8 create the second wave of the synthesized pulse P2.

The synthesized pulses P1 and P2 generated by the delays D1 to D8 are inversed, added and synthesized to obtain the output of the transmit pulse of two burst waves.

In order to obtain the output of the burst waves from the synthesized pulses P1 and P2, waveforms switched by a field-effect transistor (FET) are synthesized by using a transformer. The amplitude of the output of the burst waves is about 200 Vp-p.

However, in the prior art case in FIG. 7, obtaining two burst waves, for example, as described above, requires eight delay lines.

Furthermore, more delay lines are required for increasing the number of the burst waves for the purpose of improving the sensitivity by a transmit circuit or suppressing the second-order harmonics.

Means for increasing the number of burst waves is disclosed in Japanese Unexamined Patent Application Publication No. 2002-315749 as a technology of using a programmable delay line, feeding back a pulse delayed once to the input side and resetting the set value of the delay line to generate an arbitrary pulse length.

The technology is certainly effective for reducing the number of delay lines.

SUMMARY OF THE INVENTION

The present invention provides an ultrasonic observation apparatus connecting to an ultrasonic probe to be inserted into a body cavity, which outputs transmit signals in a pulse shape to an ultrasonic transducer internally contained in the ultrasonic probe, the apparatus including:

a secondary circuit having a ground connecting to a cabinet of the ultrasonic observation apparatus;

a patient circuit insulated in direct current from the cabinet and the ground;

a timing generating circuit provided in the secondary circuit and generating timing signals for generating the transmit signals;

an insulating circuit insulating the timing signal from the secondary circuit and transmitting the timing signal to the patient circuit; and a transmit signal generating circuit provided in the patient circuit and generating the transmit signal in synchronization with the inputted timing signal.

DETAILED DESCRIPTION OF THE PREFERRED EMBODIMENT

With reference to drawings, embodiments of the present invention will be described below.

Embodiment 1

Figure 1:
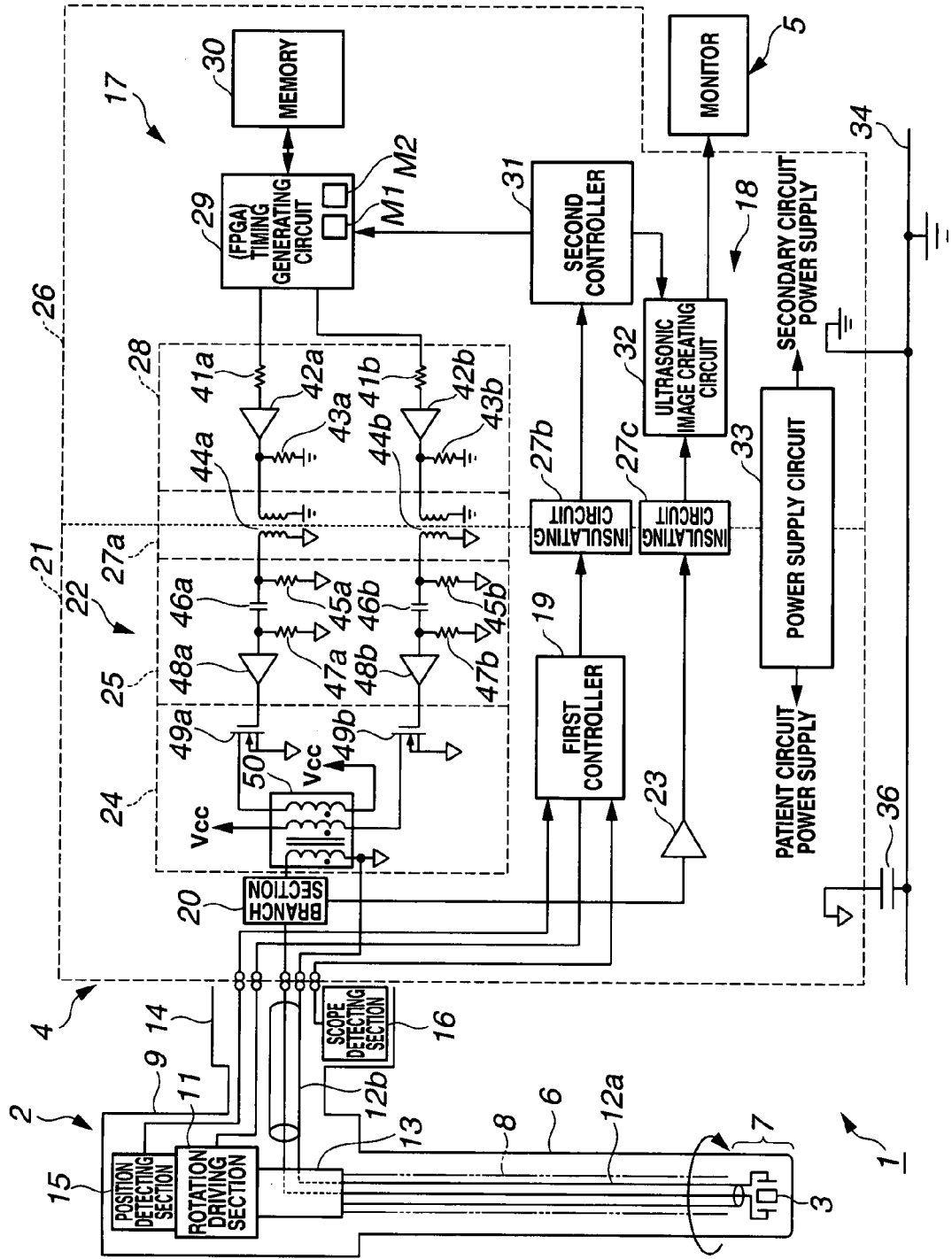
FIG. 1 is a configuration diagram showing an entire configuration of an ultrasonic diagnosis apparatus including Embodiment 1 of the present invention.
Figure 2:
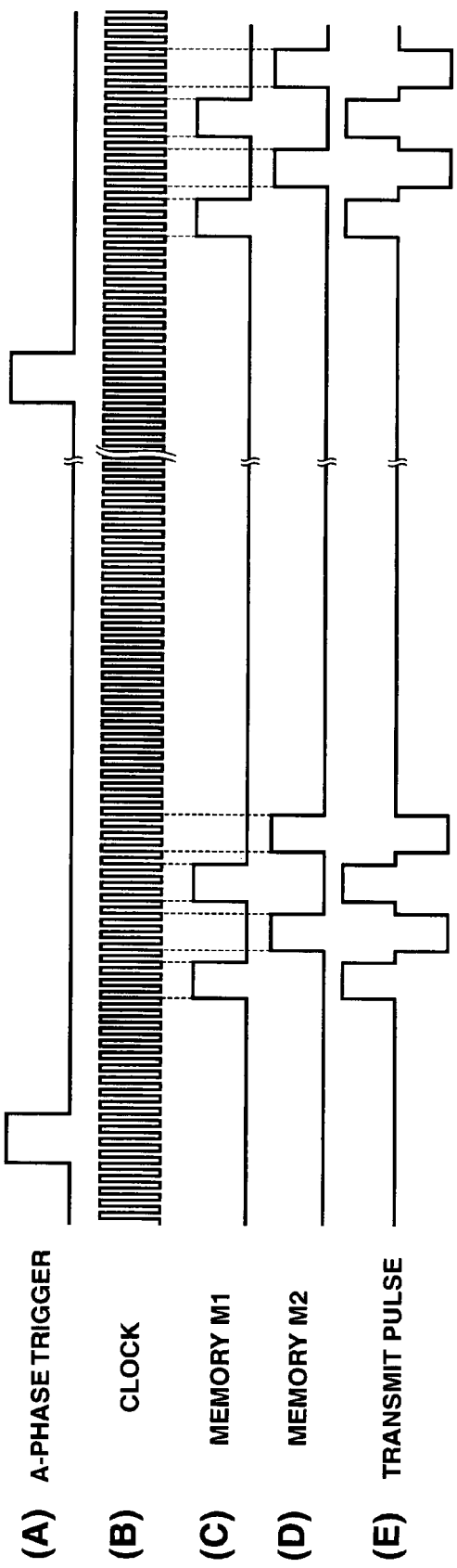
FIG. 2 is a timing chart showing operations in Embodiment 1.

With reference to FIGS. 1 and 2, Embodiment 1 of the present invention will be described. FIG. 1 shows an ultrasonic diagnosis apparatus including Embodiment 1 of the present invention.

An ultrasonic diagnosis apparatus 1 including Embodiment 1 of the present invention shown in FIG. 1 includes an ultrasonic endoscope (abbreviated to ultrasonic scope) 2, an ultrasonic endoscope observation apparatus (which will be simply abbreviated to observation apparatus) 4 of Embodiment 1, and a monitor 5. The ultrasonic scope 2 is inserted into a body cavity. The ultrasonic scope 2 is removably connected to the observation apparatus 4. The observation apparatus 4 generates drive pulses (or transmit pulses) for driving an ultrasonic transducer 3 internally contained in the ultrasonic scope 2 and performs signal processing on received ultrasonic signals. The monitor 5 displays video signals generated by the observation apparatus 4.

The ultrasonic scope 2 has a long and narrow insertion section 6 to be inserted into a body cavity. A distal end 7 of the insertion section 6 has the ultrasonic transducer 3 that transmits/receives ultrasonic wave.

The distal end 7 of the ultrasonic scope 2 in this case has illumination means and an observation optical system, not shown, for performing optical observation. FIG. 1 only shows the ultrasonic probe part.

The ultrasonic transducer 3 internally provided in the distal end 7 is mounted to the distal end of a flexible shaft 8 contained through the insertion section 6. The rear end of the flexible shaft 8 is connected to a rotation driving section 11 provided in a grasping section 9 which is provided at the rear end of the insertion section 6.

The rotation driving section 11 internally contains a motor, not shown. In response to the rotation of the motor, the rotational force is transmitted to the ultrasonic transducer 3 through the flexible shaft 8, and the ultrasonic transducer 3 rotates with the rotation of the motor.

The ultrasonic transducer 3 is connected to a rotor side contact of a slip ring 13 within the grasping section 9 through a coaxial cable 12a contained through the flexible shaft 8, for example. The rotor side contact is connected to a contact of a connector 14 through the coaxial cable 12b connecting to a stator side contact of the slip ring. The connector 14 is removably connected to the observation apparatus 4.

The rotational axis of the motor, for example, of the rotation driving section 11 within the grasping section 9 has a position detecting section 15 that detects the position of the rotational angle or amount of rotation of a rotary encoder, for example. The connector 14 has a scope detecting section 16 for detecting frequency information and writing timing information for imaging of the ultrasonic transducer 3 internally contained in the ultrasonic scope 2.

The scope detecting section 16 may generate or store an identification signal for each scope or may be constructed by connecting an identification resistance to a contact pin of the connector. By connecting the connector 14 to the observation apparatus 4, the ultrasonic transducer 3 is connected to an ultrasonic pulse generating section 17 and an ultrasonic image creating section 18 within the observation apparatus 4. The rotation driving section 11, position detecting section 15 and scope detecting section 16 are connected to a first controller 19 within the observation apparatus 4.

The ultrasonic transducer 3 of the ultrasonic scope 2 is connected to a transmitting circuit 22 and a preamplifier 23, which function as a transmit signal generating circuit, through a branch section 20 belonging to a patient circuit 21 within the observation apparatus 4. The transmitting circuit 22 has a pulse generating circuit 24, a pulse driver 25 and a first insulating circuit 27a. The pulse generating circuit 24 generates transmit signals in a pulse shape, that is, transmit pulses that drive the ultrasonic transducer 3. The pulse driver 25 drives the pulse generating circuit 24. The first insulating circuit 27a insulates and transmits a timing signal from a secondary circuit 26, which will be described later.

The first insulating circuit 27a is connected to an insulating-circuit driver 28 belonging to the secondary circuit 26. The insulating-circuit driver 28 is connected to a timing generating circuit 29 belonging to the secondary circuit 26.

The timing generating circuit 29 is connected to a memory 30 and a second controller 31.

The first controller 19 is connected to the second controller 31 through a second insulating circuit 27b that insulates and transmits an outputted signal thereof.

The preamplifier 23 that amplifies an echo signal received by the ultrasonic transducer 3 is connected to an ultrasonic image creating circuit 32 belonging to the secondary circuit 26 through a third insulating circuit 27c that insulates and transmits signals. Video signals of the ultrasonic image created by the ultrasonic image creating circuit 32 are outputted to the monitor 5, and an ultrasonic tomographic image thereof is displayed on the display of the monitor 5.

Respective power supplies, that is, the patient circuit power supply and secondary circuit power supply are provided from a power supply circuit 33 to the circuits belonging to the patient circuit 21 and the circuits belonging to the secondary circuit 26.

The ground (abbreviated to GND) of the secondary circuit 26 is directly connected to a metallic apparatus cabinet 34 of the observation apparatus 4. On the other hand, the GND of the patient circuit 21 is connected to the apparatus cabinet 34 through a high withstand voltage capacitor 36. In this way, the GND of the patient circuit 21 is insulated (floated) in direct current from the apparatus cabinet 34 and is close to conduction at low impedance with sufficiently higher frequencies than the alternate current of a commercial power supply. The apparatus cabinet 34 is grounded.

The timing generating circuit 29 generates high speed timing signals required for generating transmit pulses and outputs the signals to the first insulating circuit 27a through the insulating-circuit driver 28. The timing generating circuit 29 generates a pair of positive-pole and negative-pole pulses as timing signals in response to the generation of bipolar pulses by the pulse generating circuit 24 and outputs the pulses to the first insulating circuit 27a through the insulating-circuit driver 28 having two channels, as described later.

The insulating-circuit driver 28 having two channels includes a resistance 41a, a buffer 42a, a resistance 43a, a resistance 41b, a buffer 42b and a resistance 43b. The outputted signals of the buffers 42a and 42b are outputted to the pulse driver 25 through pulse transformers 44a and 44b included in the first insulating circuit 27a.

The pulse driver 25 also has two channels and includes a resistance 45a, a capacitor 46a, a resistance 47a, a buffer 48a, a resistance 45b, a capacitor 46b, a resistance 47b and a buffer 48b.

The outputted signals from the buffers 48a and 48b of the pulse driver 25 are outputted to the pulse generating circuit 24.

The pulse generating circuit 24 includes a power FET 49a, a power FET 49b, and a transformer 50. The power FET 49a switches a power supply voltage Vcc from OFF to ON in response to a positive outputted pulse (positive pulse). The power FET 49b switches the power supply voltage +Vcc from OFF to ON in response to a negative outputted pulse (negative pulse). The transformer 50 includes a pulse transformer in which the outputted signals of the two power FETs 49a and 49b are applied to a primary winding. Transmit pulses in a bipolar waveform, which is induced and synthesized at a secondary winding of the transformer 50, are generated, and the transmit pulses are applied to the ultrasonic transducer 3.

Based on the configuration in which the two FETs 49a and 49b are driven to output to the transformer 50, bipolar transmit signals about zero volt are generated from the transmit pulses outputted from the observation apparatus 4.

According to the present embodiment having this configuration, a pair of pulses is generated as a timing signal required for generation of a transmit pulse in the secondary circuit 26 and increasing current consumption, and the pair of pulses is transmitted to the pulse driver 25 side in the patient circuit 21 through the insulating-circuit driver 28 and insulating circuit 27a having two channels. Furthermore, a configuration is adopted in which bipolar transmit pulses are generated in the pulse generating circuit 24, which reduces the size of the circuit configuration of the patient circuit 21, reduces current consumption and effectively suppresses the occurrence of noise (radiated electromagnetic noise).

Detecting the ultrasonic scope 2 connecting to the observation apparatus 4 by using the scope detecting section 16 allows easy generation of transmit pulses at a frequency and number of pulses properly compliant with a frequency characteristic, for example, to be ultrasonically transmitted/received by the ultrasonic transducer 3 internally contained in the ultrasonic scope 2 (while the number of pulses, for example, is limited in the prior art because of the use of delay lines)

Next, operations of the components according to the present embodiment will be described.

When the ultrasonic scope 2 is connected to the observation apparatus 4, the scope detecting section 16 internally contained in the ultrasonic scope 2 can detect information such as frequency information and writing timing information for imaging of the ultrasonic transducer 3 within the connected ultrasonic scope 2.

The first controller 19 connecting to the scope detecting section 16 transmits the information to the second controller 31 through the insulating circuit 27b.

The second controller 31 instructs the timing generating circuit 29 the address of the memory 30 that stores waveform generation data for creating transmit pulses for driving the ultrasonic transducer 3.

When a scope switch on a control panel, not shown, or the ultrasonic scope 2 is operated to input a scan starting signal (unfreeze signal) to the first controller 19, the first controller 19 transmits a drive signal to the motor within the rotation driving section 11, and the motor rotates. The rotation of the motor starts rotating the ultrasonic transducer 3 within the ultrasonic scope 2 about the insertion axis, as indicated by the arrow in FIG. 1.

When the ultrasonic transducer 3 rotates, the position information (A-phase and Z-phase signals) of the ultrasonic transducer 3 is obtained by the position detecting section 15 within the ultrasonic scope 2. The A-phase signal and the Z-phase signal, which is a reference pulse, outputted once per rotation are inputted to the first controller 19, and the waveforms are shaped. Then, the signals are inputted to the second controller 31 through the insulating circuit 27b.

The A-phase and Z-phase signals are transmitted to the timing generating circuit 29 by the second controller 31 and, at the same time, are transmitted as a timing signal for the ultrasonic image creating circuit 32. The ultrasonic image creating circuit 32 performs image processing for creating an ultrasonic tomographic image from echo signals in synchronization with the timing signal.

The timing generating circuit 29 generates a basic pulse (core pulse) with a transmit pulse waveform before synthesized from the information from the scope detecting section 16 and the A-phase signal as a timing signal for transmit-pulse generation to be transmitted to the pulse generating circuit 24. The timing generating circuit 29 basically includes a field programmable gate array (abbreviated to FPGA). The FPGA uses a timing clock at a frequency of about 320 MHz.

Because of the use of the clock at about 320 MHz, the time resolution of the basic pulse functioning as a timing pulse generated by the pulse generating circuit 24 can be about 3 ns.

As described above, as the operational speed of the FPGA increases, the core voltage consumed within the FPGA and the current consumption by an IO power supply used by an external interface increase.

The core power supply and IO power supply to be consumed by the FPGA are both 2A class though also depending on the device type of the FPGA to be selected and used.

If the delay lines in the prior art are used, the current consumption is about 100 mA. On the other hand, the use of the FPGA increases the amount of the current consumption forty times.

The timing signal generated by the timing generating circuit 29 is transmitted to the insulating-circuit driver 28.

The timing signal is applied to the primary winding sides of the pulse transformers 44a and 44b of the insulating circuit 27a through the buffers 42a and 42b of the insulating-circuit driver 28 therebefore. The signal is transmitted to the secondary side winding belonging to the patient circuit 21 insulated from the secondary circuit 26 on the primary winding side and is outputted to the pulse driver 25. The outputted signal by the insulating-circuit driver 28 is a high frequency signal of a high frequency of a several MHz and is transmitted to the pulse driver 25 through the pulse transformers 44a and 44b.

In this way, the pulse transformers 44a and 44b insulate the insulating-circuit driver 28 on the secondary circuit 26 side and the pulse driver 25 belonging to the patient circuit 21. The insulation withstand voltage in direct current between the secondary circuit 26 and the patient circuit 21 by the pulse transformers 44a and 44b, for example, is about 4000 V, and the transmitting circuit 22 belonging to the patient circuit 21 is floated from the secondary circuit 26. The pulse driver 25 amplifies and shapes the transmitted pulse signal and outputs the result from the output ends of the buffers 48a and 48b to the pulse generating circuit 24.

The pulse generating circuit 24 includes the positive-pole driving FET 49a and negative-pole driving FET 49b and the transformer 50. The outputs of the FETs 49a and 49b are applied with relatively opposite phases to the primary winding of the transformer 50 and are synthesized to a bipolar output to the secondary winding.

The bipolar transmit pulse synthesized by the transformer 50 drives the ultrasonic transducer 3 accommodated within the distal end 7 of the insertion section 6 through the coaxial cable 12a, and the like, within the ultrasonic scope 2 above.

The transmitting circuit 22 belonging to the patient circuit 21 is connected to the GND by the apparatus cabinet 34 and the capacitor 36 with high withstand voltage and is defined to have a nearly equal potential as that of the apparatus cabinet 34 at high frequencies. Next, with reference to FIG. 2, details of the operations by the timing generating circuit 29 and memory 30 will be described. As described above, an A-phase signal is detected by the position detecting section 15 of the ultrasonic scope 2. The A-phase signal is shaped and transmitted to the timing generating circuit 29 as an A-phase trigger as shown in FIG. 2(A).

The timing generating circuit 29 includes an FPGA, for example, and the clock for operating the FPGA is shown in FIG. 2(B) where the frequency is about 320 MHz.

The timing generating circuit 29 stores positive and negative pole memory data for waveform generation from the memory 30 to memories M1 and M2 in the FPGA based on the signal from the scope detecting section 16.

Then, the timing generating circuit 29 sequentially outputs the memory data stored in the memories M1 and M2 as shown in FIGS. 2(C) and 2(D) to the buffers 42a and 42b of the insulating circuit driver 28 with a short time delay therebetween in a predetermined time from the A-phase trigger as a pair of positive and negative pulses for generating transmit pulses.

The signals of the pulses outputted to the buffers 42a and 42b are transmitted to the subsequent component (for generating transmit pulses) through the two channels as described above and are applied to the FETs 49a and 49b of the pulse generating circuit 24. The transformer 50 of the pulse generating circuit 24 generates a transmit pulse in a bipolar waveform as shown in FIG. 2(E), and the ultrasonic transducer 3 is driven by the transmit pulses.

Then, when the next A-phase trigger occurs after a lapse of a predetermined short period of time, the timing generating circuit 29 generates the next positive pulse and negative pulse in a predetermined time from the A-phase trigger. The pulse generating circuit 24 generates the next transmit pulses from the positive pulse and negative pulse.

The ultrasonic transducer 3 ultrasonically vibrates (ultrasonically excites) in pulse shortly in response to the application of the transmit pulses and sequentially transmits the ultrasonic wave radially by rotating the insertion axis to perform radial scanning. In this case, the ultrasonic wave is transmitted to the internal wall surface within a body cavity with which the tip 7 is in contact and is reflected by the part having different acoustic impedances. The reflected ultrasonic wave is received by the ultrasonic transducer 3 and is converted to an electric signal as an ultrasonic echo signal (which will be simply called echo signal).

The echo signal is inputted from the branch section 20, which is switched immediately after the transmission of the transmit pulses for radial transmission, to the preamplifier 23, is amplified therein, and is then inputted to the ultrasonic image creating circuit 32 belonging to the secondary circuit 26 through the insulating circuit 27c.

The ultrasonic image creating circuit 32 internally contains an A/D converting circuit and a memory and A/D converts the radially transmitted echo signals and stores the echo data to the memory. Then, the echo data for one frame by the one rotation of the radial scanning undergoes conversion processing by a digital scan converter (DSC) to display on the monitor 5, and the ultrasonic tomographic image is then displayed on the monitor 5.

By setting the data in the memory 30 to a desired value as described above, a pulse waveform and pulse length optimum for the connected ultrasonic transducer 3 can be outputted.

In other words, though FIG. 2 shows an example of the transmit pulses in a bipolar waveform of two waves, transmit pulses in a bipolar waveforms of three or more waves can be generated by changing the data within the memory 30. Furthermore, the value of the frequency of the pulse waveform can be changed.

The timing generating circuit 29 operates at a significantly high clock speed, and the current consumption increases. However, the timing generating circuit 29 is provided in the secondary circuit 26, and the GND is connected to the apparatus cabinet 34 of the observation apparatus 4. Therefore, the radiated electromagnetic noise can be significantly small.

The amount of the radiated electromagnetic noise can be reduced by bringing the transmitting circuit 22 belonging to the patient circuit 21 into conduction in high frequencies with the apparatus cabinet 34 through the capacitor 36 having high withstand voltage to be stabilized at the GND potential.

Like the configuration, by providing the timing generating circuit 29 consuming a large amount of power within the secondary circuit 26, the transmission pulses at an arbitrary frequency and number of pulses (pulse length) can be generated. Thus, the size of the observation apparatus 4 can be decreased without increasing the amount of the radiated electromagnetic noise.

In conclusion, the present embodiment has following effects.

A transmission output at an arbitrary frequency and a number of pulses (pulse length) can be obtained while reducing the size of the circuit.

The current consumption of the patient circuit 21 to which the ultrasonic scope 2 is connected can be reduced, and the occurrence of the radiated electromagnetic noise by handling the ultrasonic scope 2 belonging to the patient circuit 21 as an antenna can be reduced.

Providing the timing generating circuit, which has been provided in a patient circuit in the prior art, in the secondary circuit, can reduce the size of the configuration of the patient circuit and the size of the observation apparatus body.

The necessity for using many delay lines like conventional cases can be eliminated, which can reduce the costs.

Embodiment 2

Figure 3:
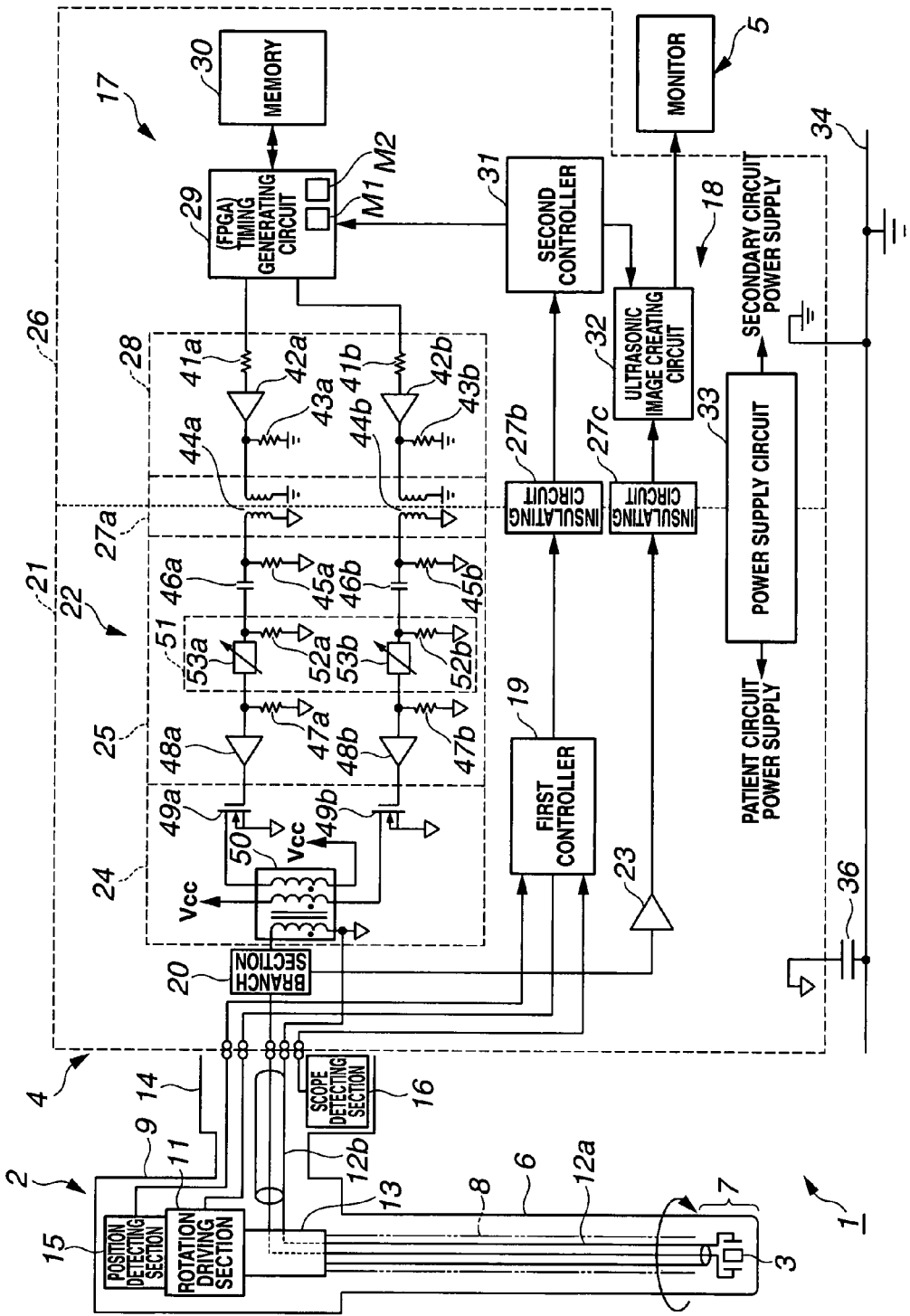
FIG. 3 is a configuration diagram showing an entire configuration of an ultrasonic diagnosis apparatus including Embodiment 2 of the present invention.
Figure 4:
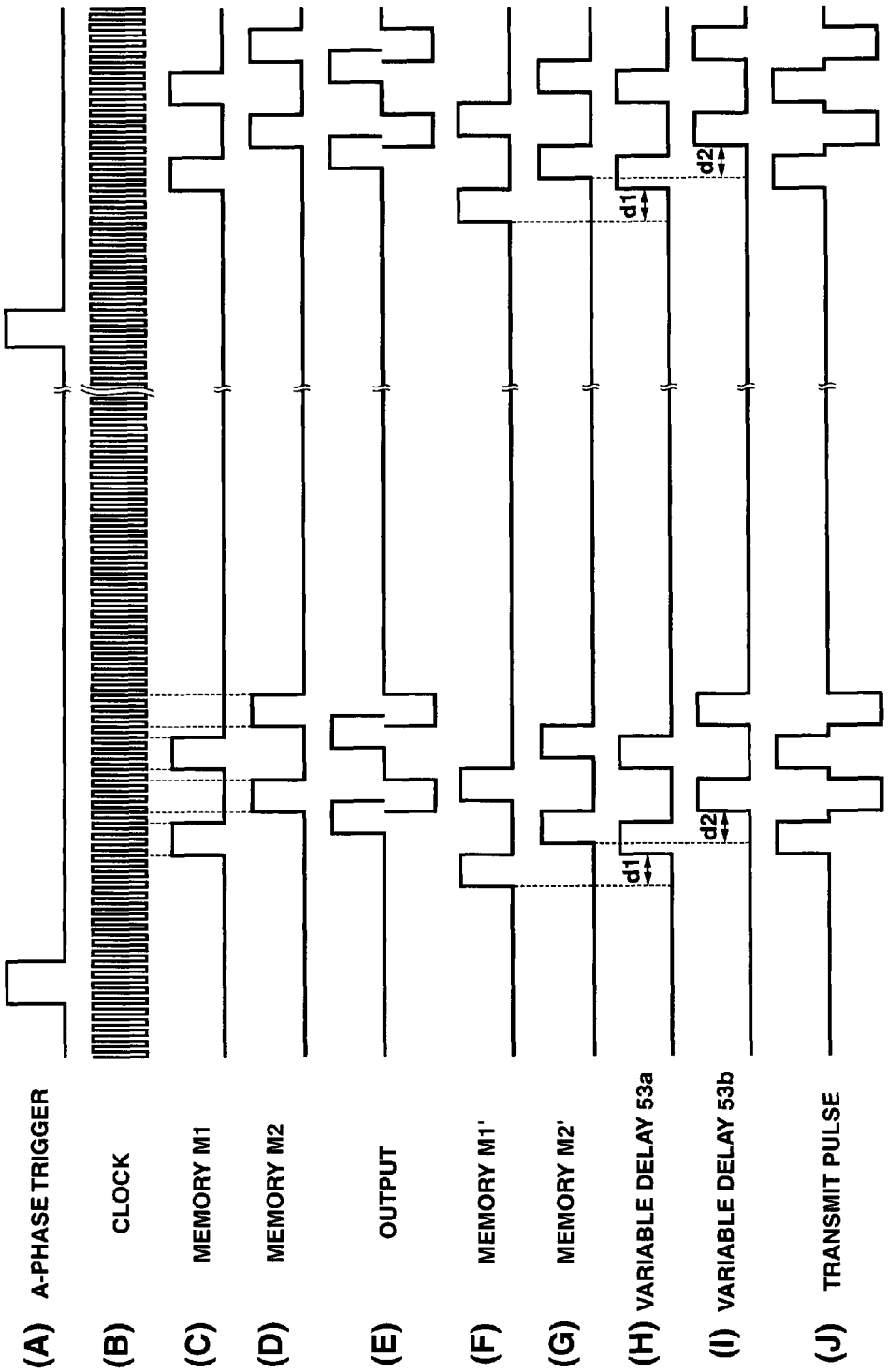
FIG. 4 is a timing chart showing operations in Embodiment 2.

With reference to FIGS. 3 and 4, Embodiment 2 of the present invention will be described next. FIG. 3 shows an entire configuration of an ultrasonic diagnosis apparatus 1 including Embodiment 2 of the present invention. The ultrasonic diagnosis apparatus 1 shown in FIG. 3 includes a timing adjusting circuit 51 that adjusts timing for positive pulse and negative pulse (by using a delay time) in the pulse driver 25 included in the transmitting circuit 22 in the ultrasonic diagnosis apparatus 1 in FIG. 1.

More specifically, the other end of the capacitor 46a serially connecting to one end of the secondary wiring of the pulse transformer 44a is grounded through a resistance 52a and is connected to the input end of the buffer 48a through a variable delay 53a with a variable amount of delay.

The other end of the capacitor 46b serially connecting to one end of the secondary wiring of the pulse transformer 44b is grounded through a resistance 52b and is connected to the input end of the buffer 48b through a variable delay 53b with a variable amount of delay.

The rest of the configuration is the same as that of Embodiment 1, and the description on the same components will be omitted herein.

Though FIG. 3 shows the configuration including the timing adjusting circuit 51 within the pulse driver 25, the timing adjusting circuit 51 may be provided between the insulating circuit 27a and the pulse driver 25.

The present embodiment is configured to address a case that the positive pulse and negative pulse have different amounts of delay in the path from the timing generating circuit 29 to the pulse generating circuit 24.

With reference to FIG. 4, details of the operation of the present embodiment will be described next.

FIGS. 4(C) to 4(E) of FIG. 4 show a case that no transmit pulses (output), which are not intended, can be obtained because the positive pulse and the negative pulse have different amounts of delay. Also in this case, by providing the timing adjusting circuit 51, proper transmit pulses can be obtained as shown in FIG. 4(J).

Like Embodiment 1, by handling the A-phase trigger in FIG. 4(A) as a synchronizing signal, the timing generating circuit 29 including an FPGA reads positive memory data and negative memory data in the memory 30 and stores them in the memories M1 and M2 in the FPGA in synchronization with the clock in FIG. 4(B).

Then, by handling the A-phase trigger as a synchronizing signal, the data is read from the memories M1 and M2 as shown in FIGS. 4(C) and 4(D) at a predetermined time, and the positive pulse and negative pulse are outputted to the insulating-circuit driver 28 side.

The insulating circuit driver 28 applies the positive pulse and the negative pulse to the pulse driver 25 through the insulating circuit 27a. The pulse driver 25 transmits the transmitted positive pulse and negative pulse to the pulse generating circuit 24. The output of the transmit pulses is generated by the pulse generating circuit, but the timings of the positive pulse and negative pulse may be different due to the influence of the path from the timing generating circuit 29 to the pulse generating circuit 24.

If the propagation path of the two channels have different amounts of delay like a large amount of delay for a positive pulse and a small amount of delay for a negative pulse, the output (transmit pulses) in a waveform shown in FIG. 4(E) is obtained, meaning that the intended waveform cannot be obtained.

The present embodiment allows solving the problem in this case. If the propagation paths for positive pulses and negative pulses have different amounts of delay as described above, the correction is performed in the following steps.

If a propagation delay occurs in the path from the timing generating circuit 29 to the pulse generating circuit 24, the output timings of the memories M1 and M2 are corrected like memories M1' and M2' shown in FIGS. 4(F) and 4(G) (that is, the timings of the occurrence (output) of the positive pulses and negative pulses are defined earlier).

Next, the amounts of delay for the positive pulses and negative pulses are adjusted by the timing adjusting circuit 51 such that the transmit pulses outputted by the pulse generating circuit 24 can have the waveform in FIG. 4(J). For example, the positive pulses are delayed by d1 by the variable delay 53*a* as shown in FIG. 4(H), and the negative pulses are delayed by d2 by the variable delay 53*b* as shown in FIG. 4(I) so that transmit pulses in a desired waveform can be obtained.

This configuration allows proper correction of the difference in propagation delay by the timing adjusting circuit 51 even when the timing generating circuit 29 consuming a large current is provided in the secondary circuit 26 and the two channels have different propagation delays in the propagation path from the timing generating circuit 29 to the patient circuit 21.

The timing adjusting circuit 51 can be implemented by a significantly small circuit since a large amount of delay is not required.

Furthermore, the amount of the radiated electromagnetic noise is not increased since the power consumption is not changed very much.

In addition to the effects of Embodiment 1, the present embodiment can advantageously address even the case where the positive pulses and negative pulses have different amounts of delay in the path from the timing generating circuit 29 to the pulse generating circuit 24.

Embodiment 3

Figure 5:
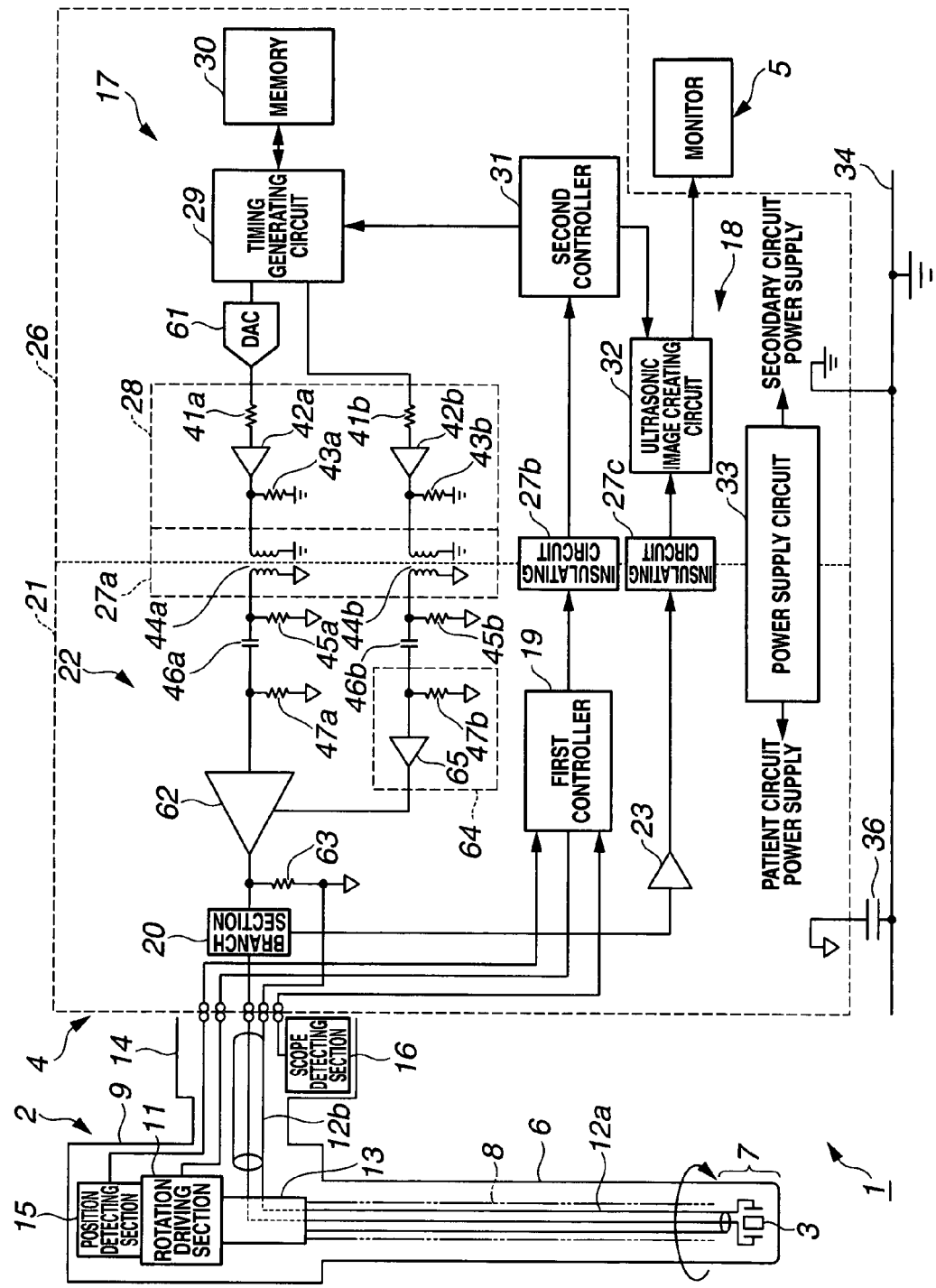
FIG. 5 is a configuration diagram showing an entire configuration of an ultrasonic diagnosis apparatus including Embodiment 3 of the present invention.
Figure 6:
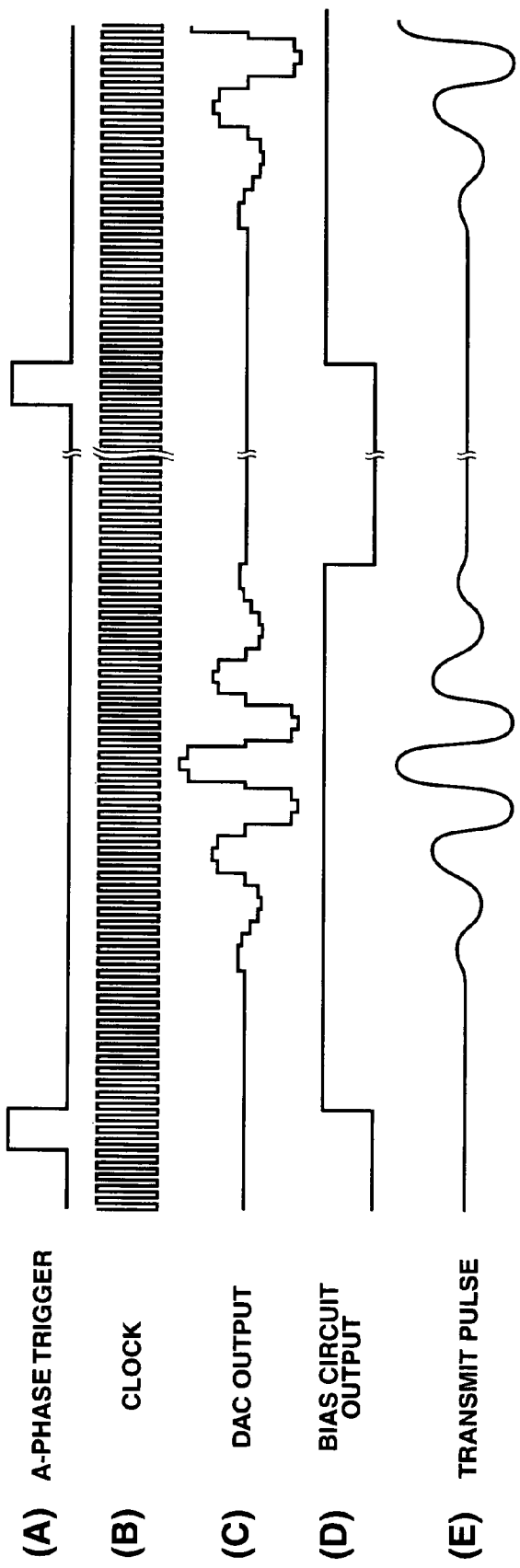
FIG. 6 is a timing chart showing operations in Embodiment 3.
Figure 7:
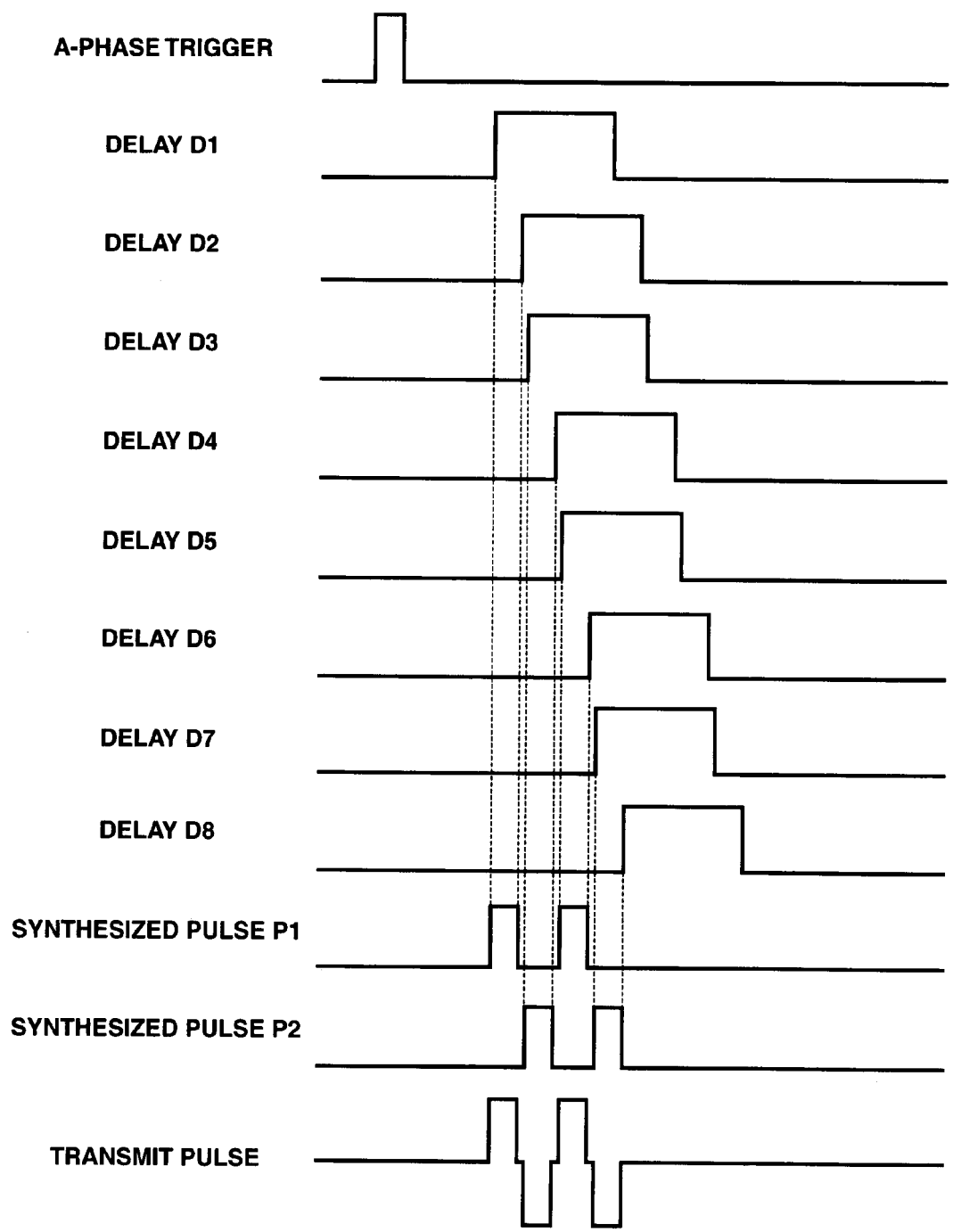
FIG. 7 is a timing chart showing a process of creating a transmit waveform in a prior art.

With reference to FIGS. 5 and 6, Embodiment 3 of the present invention will be described next. FIG. 5 shows an entire configuration of an ultrasonic diagnosis apparatus including Embodiment 3.

In the ultrasonic diagnosis apparatus 1, the timing generating circuit 29 generates timing signals of two channels as in the ultrasonic diagnosis apparatus 1 of the Embodiment 1. The ultrasonic diagnosis apparatus 1 further includes a DAC circuit 61, which converts digital signals to analog signals, that is, D/A converts, is connected to a first channel side of the two channels. The outputted signal of the DAC circuit 61 is inputted along with the signal of the second channel side outputted from the timing generating circuit 29 to the insulating-circuit driver 28.

According to the present embodiment, an amplifier 62 is connected to the output end of the first channel side in the insulating circuit 27*a* through the capacitor 46*a*, for example.

The output end of the amplifier 62 is connected to a matching resistance 63 and is connected to the ultrasonic transducer 3 of the ultrasonic scope 2 through the branch section 20. The ultrasonic transducer 3 is driven by the transmit pulses outputted from the amplifier 62.

On the other hand, the other outputted signal of the timing generating circuit 29 is inputted to a bias circuit 64 provided within the patient circuit 21 through the insulating-circuit driver 28 and the insulating circuit 27*a*. The bias circuit 64 includes a buffer circuit 65, for example. The outputted signal of the bias circuit 64 is connected to a bias terminal that controls an amplifying operation by the amplifier 62.

Then, the bias circuit 64 generally applies a signal of "L"-level to the bias terminal to define the amplifier 62 not to perform the amplifying operation. During a period where transmit signals occur, the bias circuit 64 applies a signal of "H"-level to the bias terminal to define to perform the amplifying operation. In other words, the other outputted signal (second signal) outputted by the timing generating circuit 29 functions as a control signal that controls the operation by the amplifier 62 included in the transmitting circuit 22.

The present embodiment configures the ultrasonic transducer 3 to be capable of generating transmit pulses (transmit signals) in a waveform having a less harmonic component. For this reason, the timing generating circuit 29 transmits signals in a transmit pulse waveform to the transmitting circuit 22 side through one channel and transmits a control signal that operates the amplifier 62 of the transmitting circuit 22 through the other channel during a period for generating transmit pulses.

According to the present embodiment, the power supply circuit 33 functions as a bipolar patient circuit power supply (though only functions as a positive (single pole) patient circuit power supply in Embodiments 1 and 2). The power supply circuit 33 can output in a bipolar manner also through the secondary circuit power supply (though only functions as a positive (single pole) secondary circuit power supply in Embodiment 1 and 2).

With reference to FIG. 6, operations of the present embodiment will be described next.

Like Embodiment 1 as described above, a transmit pulse is obtained in synchronization with an A-phase trigger. FIG. 6(A) shows the A-phase trigger. The timing generating circuit 29 includes an FPGA that operates at a clock speed of about 320 MHz shown in FIG. 6(B) like Embodiment 1.

The FPGA reads memory data stored in the memory 30.

While the memory data is data descriptions of one bit in Embodiment 1, the memory data in the present embodiment is data descriptions of 8 bits.

The memory data in the memory 30, which is read once by the FPGA, is outputted in 8 bits in synchronization with the clock after a lapse of a predetermined period of time from the A-phase trigger.

The memory data of 8 bits outputted from the FPGA can have an amplitude in an arbitrary waveform through the DAC circuit 61 like the DAC output in FIG. 6(C).

At the same time, the FPGA (that is, the timing generating circuit 29) generates, as the other output, a bias circuit output functioning as a control signal (for the amplifier 62) to be outputted to the bias circuit 64 as shown in FIG. 6(D).

The bias circuit output is generated by the timing generating circuit 29 by reading the data from the memory 30, for example.

The DAC output and the bias circuit output are applied to the amplifier 62 in the patient circuit 21 through the insulating-circuit driver 28 and the insulating circuit 27*a*.

The amplifier 62 is generally at OFF state for most of time without the application of the bias circuit output (at an output level equal to zero or "L"-level) and does not perform an amplifying operation. In response to the application of the bias circuit output shown in FIG. 6(D) by the bias circuit 64, bias current flows into the amplifier 62, and the amplifier 62 is enabled to perform an amplifying operation.

As described above, after the bias circuit output is supplied to the amplifier 62 as a preceding control signal, the DAC output shown in FIG. 6(C) is applied to the amplifier 62.

The amplifier 62 linearly amplifies the signal inputted through the DAC circuit 61 to have an amplitude of about 200 Vpp.

The amplified transmit output is applied to the ultrasonic transducer 3 of the ultrasonic scope 2 as transmit pulses, and ultrasonic wave is excited.

The transmit pulses in FIG. 6(E) are drive signals to be applied to the ultrasonic transducer 3, and the transmit pulses can have a transmit waveform resulting from the suppression of harmonics of the pulse waveform of the fundamental waves by several tens dB.

In other words, according to the present embodiment, the high harmonic component of a transmit waveform can be largely reduced even when a broadband ultrasonic transducer 3 is used.

The high harmonic component of a receive signal returned from a subject can be received and converted to an echo signal efficiently by the broadband transducer 3, which significantly increases the sensitivity for creating an image of THI.

Therefore, in the ultrasonic image creating circuit 32 according to the present embodiment, the processing of creating an ultrasonic image based on fundamental waves can be performed from the echo signals received and obtained by the ultrasonic transducer 3, and an ultrasonic image with a high lateral resolution can be obtained by extracting and imaging the signal component of second or third-order harmonics of fundamental waves of the echo signals to suppress the side lobe.

According to the present embodiment, by performing ON/OFF control over the operation of the amplifier 62 by the bias circuit 64, the transmitting circuit 22 can be configured with minimum and necessary power consumption, and the size of the patient circuit 21 can be reduced, which reduces the size of the circuits of the observation apparatus 4 and can reduce the size and costs.

The current consumption can be reduced, which can reduce the amount of radiated noise.

According to the present embodiment, in addition to the effects of Embodiment 1, transmit pulses can be generated in a pulse waveform suitable for a characteristic of the ultrasonic transducer 3 internally contained in the ultrasonic scope 2 connecting to the observation apparatus 4 (in other words, in a substantially arbitrary pulse waveform).

The present embodiment has an effect that allows improvement of the sensitivity of THI since harmonics can be suppressed in the waveform of transmit pulses.

Furthermore, weighting can be performed with a window function such as Gaussian window, which can contribute to the suppression of side lobes and improvement of the resolution.

Having described the case with the ultrasonic scope 2, the present invention is also applicable to an ultrasonic probe only including the ultrasonic transducer 3 without any optical observation means in the distal end 7 of the insertion section 6.

In the embodiments above, another capacitor in addition to the capacitor 36 and a switch, which is serially connected to the capacitor for switching ON/OFF the connection to the apparatus cabinet 34, may be provided. Thus, the connection to the apparatus cabinet 34 may be switched OFF during a period when transmit pulses occur and be switched ON during a period when processing on echo signals is performed after the output of transmit pulses.

In other words, during a period when processing is performed on echo signals after the output of transmit pulses, the GND of the patient circuit 21 is brought into conduction at high frequencies by the impedance by the capacitor 36, and the GND of the patient circuit 21 is brought into conduction at high frequencies by another capacitor. Then, the external intrusion of noise can be reduced during an operation for creating an ultrasonic image in signal processing on echo signals such that an ultrasonic image with a high S/N can be created.

As described above, according to the present invention, the size of the circuit and the amount of radiated electromagnetic noise can be reduced, and transmit signals can be generated in an arbitrary waveform (with a few restrictions for waveforms) suitable for driving an ultrasonic transducer.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic observation apparatus connecting to an ultrasonic probe to be inserted into a body cavity, which outputs transmit signals in a pulse shape to an ultrasonic transducer internally contained in the ultrasonic probe, the apparatus comprising:

a secondary circuit having a ground connecting to a cabinet of the ultrasonic observation apparatus;

a patient circuit insulated in direct current from the cabinet and the ground;

a timing signal generating circuit provided in the secondary circuit and generating timing signals for generating the transmit signals;

an insulating circuit with two channels including a first insulating circuit and a second insulating circuit insulating the timing signals from the secondary circuit and transmitting the timing signals to the patient circuit; and a transmit signal generating circuit provided in the patient circuit and generating the transmit signals in synchronization with the inputted timing signals, wherein the timing signal generating circuit generates multiple pieces of digital signal data for creating the transmit signals and includes a digital-analog converting circuit for generating analog first signals in a waveform compliant with the transmit signals from the multiple pieces of digital signal data;

the first insulating circuit insulates and transmits the first signals so as to be inputted to an amplifying circuit included in the transmit signal generating circuit; and the second insulating circuit controls turning on and off the amplifying circuit such that the amplifying circuit performs amplification only in the vicinity of the period when the first signals are inputted to the amplifying circuit by transmitting second signals generated by the timing signal generating circuit in synchronization with the first signals and applying the transmitted second signals to the amplifying circuit.

2. The ultrasonic observation apparatus according to claim 1, wherein the timing signal generating circuit generates a pair of timing pulses for generating the transmit signals.

3. The ultrasonic observation apparatus according to claim 1, wherein the amplifying circuit generates the transmit signals in a bipolar waveform from the first signals inputted through the insulating circuit.

4. The ultrasonic observation apparatus according to claim 1, wherein the patient circuit has a ground connecting to the cabinet through a capacitor.

5. The ultrasonic observation apparatus according to claim 1, further comprising an information detecting unit for detecting information about the ultrasonic transducer of the ultrasonic probe connecting to the ultrasonic observation apparatus.

6. The ultrasonic observation apparatus according to claim 5, further comprising a control circuit controlling the timing signals generated by the timing signal generating circuit from the information detected by the information detecting unit.

7. The ultrasonic observation apparatus according to claim 1, wherein the timing signal generating circuit has a memory for storing pulse data for generating multiple kinds of pulse waveforms as the timing signals.

8. The ultrasonic observation apparatus according to claim 1, wherein the timing signal generating circuit has a field programmable gate array.

* * * * *